(12) United States Patent
Beardsley et al.

(10) Patent No.: US 9,636,091 B2
(45) Date of Patent: May 2, 2017

(54) HAND-HELD ELECTROMECHANICAL SURGICAL SYSTEM

(71) Applicant: Covidien LP, Mansfield, MA (US)

(72) Inventors: John Beardsley, Wallingford, CT (US); Matthew Chowaniec, Middletown, CT (US); Russell Pribanic, Roxbury, CT (US); Paul Rinaldi, Wolcott, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/983,689

(22) Filed: Dec. 30, 2015

(65) Prior Publication Data
US 2016/0106401 A1 Apr. 21, 2016

Related U.S. Application Data

(63) Continuation-in-part of application No. 14/865,843, filed on Sep. 25, 2015, now Pat. No. 9,456,873, which
(Continued)

(51) Int. Cl.
*A61B 18/18* (2006.01)
*A61B 17/00* (2006.01)
(Continued)

(52) U.S. Cl.
CPC ............ *A61B 17/00* (2013.01); *A61B 17/068* (2013.01); *A61B 17/07207* (2013.01);
(Continued)

(58) Field of Classification Search
CPC ........ A61B 5/15188; A61B 2017/2931; A61B 2017/2925; A61B 2017/0046
See application file for complete search history.

(56) References Cited

U.S. PATENT DOCUMENTS 5,230,704 A 7/1993 Moberg et al.
5,499,992 A 3/1996 Meade et al.
(Continued)

FOREIGN PATENT DOCUMENTS

CN 102028509 A 4/2011
EP 0804124 B1 11/1997
(Continued)

OTHER PUBLICATIONS

Chinese Office Action (with English translation) dated Dec. 25, 2015, corresponding to Chinese Application No. 201310012945.0; 16 total pages.
(Continued)

*Primary Examiner* — Robert N Wieland

(57) ABSTRACT

A hand-held electromechanical surgical device is configured to selectively connect with a surgical accessory. The surgical device includes a power-pack, an outer shell housing, and a gasket. The power-pack is configured to selectively control a surgical accessory. The outer shell housing includes a distal half-section and a proximal half-section, the distal half-section and the proximal half-section together defining a cavity configured to selectively encase substantially the entire power-pack therein. The gasket is located between the distal half-section and the proximal half-section of the outer shell housing. The gasket is configured to create a seal between the distal half-section and the proximal half-section and to provide a sterile barrier between the power-pack and an outside environment outside the outer shell housing.

14 Claims, 13 Drawing Sheets

Related U.S. Application Data is a continuation of application No. 14/551,321, filed on Nov. 24, 2014, now Pat. No. 9,155,529, which is a continuation of application No. 13/719,344, filed on Dec. 19, 2012, now Pat. No. 8,894,647.

(60) Provisional application No. 61/586,201, filed on Jan. 13, 2012.

(51) Int. Cl.
| | |
|---|---|
| *A61B 17/068* | (2006.01) |
| *A61B 17/072* | (2006.01) |
| *A61B 17/32* | (2006.01) |
| *A61B 17/3201* | (2006.01) |
| *A61B 90/70* | (2016.01) |
| *A61B 17/29* | (2006.01) |
| *A61B 90/00* | (2016.01) |

(52) U.S. Cl.
CPC .......... *A61B 17/32* (2013.01); *A61B 17/3201* (2013.01); *A61B 90/70* (2016.02); *A61B 2017/00017* (2013.01); *A61B 2017/0046* (2013.01); *A61B 2017/00115* (2013.01); *A61B 2017/00398* (2013.01); *A61B 2017/00477* (2013.01); *A61B 2017/00526* (2013.01); *A61B 2017/00734* (2013.01); *A61B 2017/00907* (2013.01); *A61B 2017/2925* (2013.01); *A61B 2090/0813* (2016.02)

(56) References Cited

U.S. PATENT DOCUMENTS

| | | | |
|---|---|---|---|
| 5,746,759 | A | 5/1998 | Meade et al. |
| 5,752,972 | A | 5/1998 | Hoogeboom |
| 5,928,255 | A | 7/1999 | Meade et al. |
| 5,931,849 | A | 8/1999 | Desvignes et al. |
| 6,206,844 | B1 | 3/2001 | Reichel et al. |
| 7,468,041 | B2 | 12/2008 | Rhodes et al. |
| 8,221,449 | B2 | 7/2012 | Gadberry et al. |
| 8,894,647 | B2 | 11/2014 | Beardsley et al. |
| 9,155,529 | B2 | 10/2015 | Beardsley et al. |
| 2004/0116952 | A1 | 6/2004 | Sakurai et al. |
| 2006/0226195 | A1 | 10/2006 | Scirica et al. |
| 2008/0077149 | A1 | 3/2008 | Hoegerle |
| 2010/0057106 | A1 | 3/2010 | Sorrentino et al. |
| 2011/0017801 | A1 | 1/2011 | Zemlok et al. |
| 2011/0112517 | A1 | 5/2011 | Peine et al. |
| 2011/0125138 | A1 | 5/2011 | Malinouskas et al. |
| 2011/0306952 | A1 | 12/2011 | Chen et al. |
| 2012/0116266 | A1 | 5/2012 | Houser et al. |
| 2012/0238829 | A1 | 9/2012 | Shelton, IV et al. |
| 2012/0239010 | A1 | 9/2012 | Shelton, IV et al. |
| 2012/0253116 | A1 | 10/2012 | Sniffin et al. |
| 2012/0253328 | A1 | 10/2012 | Cunningham et al. |
| 2013/0072952 | A1* | 3/2013 | Storz ............ A61B 17/1626 606/178 |
| 2016/0008080 | A1 | 1/2016 | Beardsley et al. |

FOREIGN PATENT DOCUMENTS

| | | |
|---|---|---|
| JP | H09538 A | 1/1997 |
| JP | 2000254141 A | 9/2000 |
| JP | 2010051805 A | 3/2010 |
| JP | 2011078772 A | 4/2011 |

OTHER PUBLICATIONS

European Search Report, dated Mar. 13, 2015, corresponding to European Application No. 13 15 1037.2; 7 pages.

Chinese First Office Action (with English translation), dated Jan. 26, 2016, corresponding to Chinese Application No. 201310013044.3; 16 total pages.

Chinese Second Office Action (with English translation), dated Aug. 4, 2016, corresponding to Chinese Application No. 201310012945.0; 18 total pages.

Japanese Office Action (with English translation), dated Aug. 30, 2016, corresponding to Japanese Application No. 2013-000854; 8 total pages.

Australian Patent Examination Report No. 1, dated Sep. 5, 2016, corresponding to Australian Application No. 2013200115; 3 pages.

European Search Report dated Feb. 8, 2017, corresponding to European Application No. 16179552.1; 11 pages.

* cited by examiner

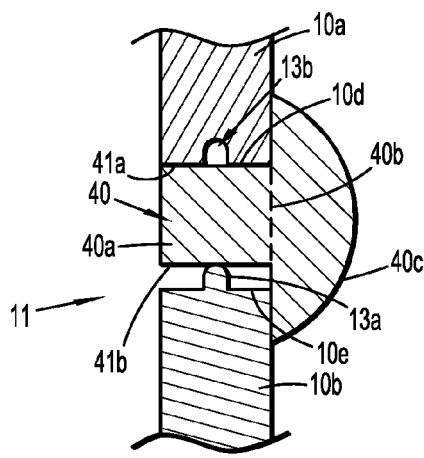
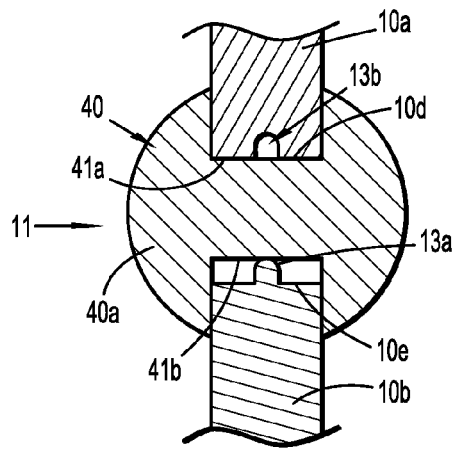
FIG. 5A  FIG. 5B
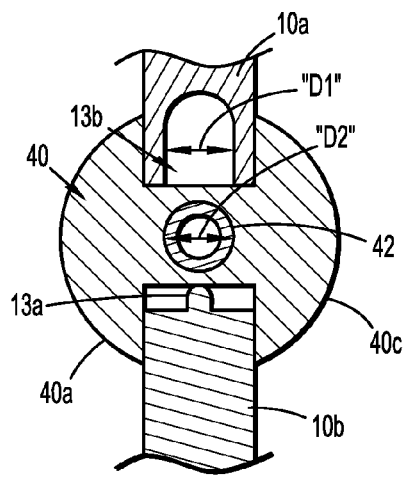
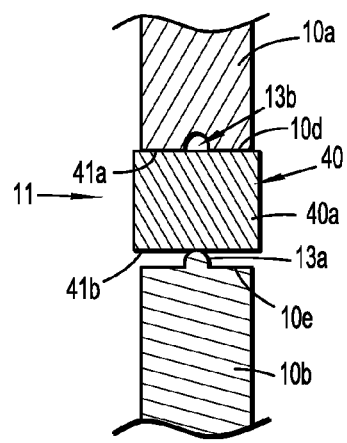
FIG. 5C  FIG. 5D
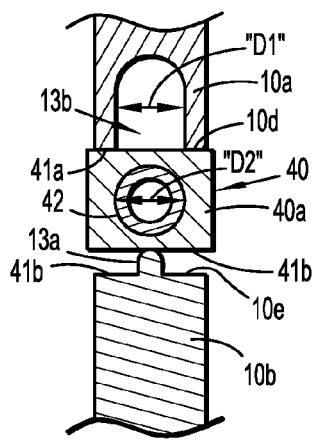
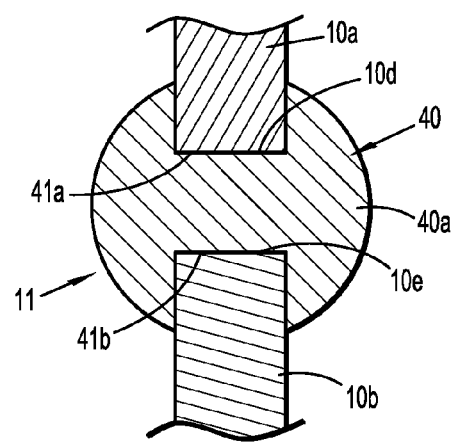
FIG. 5E  FIG. 5F

HAND-HELD ELECTROMECHANICAL SURGICAL SYSTEM

CROSS REFERENCE TO RELATED APPLICATIONS

The present application is a Continuation-in-Part of U.S. patent application Ser. No. 14/865,843, filed on Sep. 25, 2015, (now U.S.Pat. No. 9,456,873), which is a Continuation Application of U.S. patent application Ser. No. 14/551,321, filed on Nov. 24, 2014, (now U.S. Pat. No. 9,155,529), which is a continuation of U.S. patent application Ser. No. 13/719,344, filed on Dec. 19, 2012, (now U.S. Pat. No. 8,894,647), which claims the benefit of and priority to U.S. Provisional Patent Application Ser. No. 61/586,201, filed on Jan. 13, 2012, the entire contents of each of which are incorporated by reference herein.

The present application relates to U.S. patent application Ser. No. 13/719,377,filed Dec. 19, 2012, (now U.S. Pat. No. 9,241,757), the entire contents of which are incorporated by reference herein.

BACKGROUND

1. Technical Field

The present disclosure relates to surgical devices. More specifically, the present disclosure relates to hand-held electromechanical surgical systems for performing surgical procedures.

2. Background of Related Art

Generally, a hand-held electromechanical surgical system includes a powered handle assembly, which is reusable, and a disposable end effector or the like that is selectively connected to the powered handle assembly prior to use and then disconnected from the powered handle assembly following use in order to be disposed of or in some instances sterilized for re-use. The powered handle assembly may include a sterile outer shell housing and a power-pack selectively loadable into the outer shell housing.

In order to maintain a sterile environment in the operating room, a need exists for a shell housing incorporating an improved seal between the power-pack and the operating room.

SUMMARY

According to an aspect of the present disclosure, a hand-held electromechanical surgical device configured to selectively connect with a surgical accessory includes a power-pack, an outer shell housing, and a gasket. The power-pack is configured to selectively control a surgical accessory. The outer shell housing includes a distal half-section and a proximal half-section, the distal half-section and the proximal half-section together defining a cavity configured to selectively encase substantially the entire power-pack therein. The gasket is located between the distal half-section and the proximal half-section of the outer shell housing, the gasket configured to create a seal to provide a sterile barrier between the power-pack and an outside environment.

The distal half-section may include a proximal facing edge and the proximal half-section may include a distal facing edge. In a first position, the proximal facing edge and the distal facing edge are spaced apart, and in a second position, the proximal facing edge and the distal facing edge are approximated defining an interface therebetween. The gasket may be disposed at the interface defined between the distal facing edge of the proximal half-section of the outer shell housing, and the proximal facing edge of the distal half-section of the outer shell housing.

The proximal facing edge of the distal half-section of the outer shell housing may define a groove configured to receive the gasket. The distal facing edge of the proximal half-section may define a protrusion configured to engage the gasket, such that in the second position, at least a portion of the gasket is nested in the groove defined in the distal half-section when the proximal half-section and the distal half-section are approximated.

The gasket may include a reinforcing member configured to strengthen the seal between the distal half-section and the proximal half-section. The reinforcing member may be configured to be nested in the groove defined in the distal half-section of the outer shell housing when the proximal half-section and the distal half-section are approximated.

An insertion guide positionable on the distal facing edge of the proximal half-section of the outer shell housing may be provided with the electromechanical surgical device. The insertion guide is configured to shield an outer surface of the outer shell housing from the power-pack when the power-pack is being inserted into the cavity of the outer shell housing. The insertion guide may include a body defining a track, the track configured to engage the distal facing edge of the proximal half-section of the outer shell. The gasket may be locatable in the track of the insertion guide, such that, when the insertion guide is disposed on the distal facing edge of the proximal half-section of the outer shell housing, the gasket is disposed on the distal facing edge of the proximal half-section of the outer shell housing. The insertion guide may include a mechanical release configured to release the gasket from the track.

According to an aspect of the present disclosure, a method of assembling a hand-held electromechanical surgical device includes providing a hand-held electromechanical surgical device including an outer shell housing, installing a gasket onto the outer shell housing, inserting the power-pack into a receiving cavity of the outer shell housing while maintaining a sterility of the outer shell housing, and closing the outer shell housing to encase the power-pack therein.

Installing the gasket onto the outer shell housing may include removing a removable coating from a second side of the gasket and locating the second side of the gasket on a proximal half-section of the outer shell housing. Installing the gasket onto the outer shell housing may further include inserting the gasket into a track defined in an insertion guide configured to guide the insertion of the power-pack into the receiving cavity of the outer shell housing, locating the insertion guide onto a proximal half-section of the outer shell housing such that the gasket is located on a distal facing edge of the proximal half-section of the outer shell housing, and releasing the gasket from the track defined in the insertion guide such that when the insertion guide is removed from the proximal half-section of the outer shell housing, the gasket remains located on the distal facing edge of the proximal half-section of the outer shell housing.

According to an aspect of the present disclosure, a kit including a power-pack, an electromechanical surgical device, and an insertion guide is provided. The electromechanical surgical device includes an outer shell housing having a distal half-section and a proximal half-section, the distal half-section and the proximal half-section together defining a cavity configured to selectively encase substantially the entire power-pack therein. The insertion guide is locatable on the distal facing edge of the proximal half-section of the outer shell housing, the insertion guide configured to shield an outer surface of the outer shell housing from the power-pack when the power-pack is being inserted into the cavity of the outer shell housing.

The insertion guide may include a body defining a track, the track configured to engage the distal facing edge of the proximal half-section of the outer shell.

The kit may also include a gasket, wherein the gasket is positioned in the track of the insertion guide, such that when the insertion guide is disposed on the distal facing edge of the proximal half-section of the outer shell housing, the gasket is disposed on the distal facing edge of the proximal half-section of the outer shell housing.

The insertion guide may include a mechanical release configured to release the gasket from the track therein.

BRIEF DESCRIPTION OF THE DRAWINGS

Embodiments of the present disclosure are described herein with reference to the accompanying drawings, wherein:

FIG. 5A is a cross-sectional view of another embodiment of an interface defined in the outer shell housing of an electromechanical hand-held surgical device;

FIG. 5B is a cross-sectional view of yet another embodiment of an interface defined in the outer shell housing of an electromechanical hand-held surgical device;

FIG. 5C is a cross-sectional view of still another embodiment of an interface defined in the outer shell housing of an electromechanical hand-held surgical device;

FIG. 5D is a cross-sectional view of a further embodiment of an interface defined in the outer shell housing of an electromechanical hand-held surgical device;

FIG. 5E is a cross-sectional view of another embodiment of an interface defined in the outer shell housing of an electromechanical hand-held surgical device;

FIG. 5F is a cross-sectional view of yet another embodiment of an interface defined in the outer shell housing of an electromechanical hand-held surgical device;

DETAILED DESCRIPTION OF EMBODIMENTS

Figure 1:
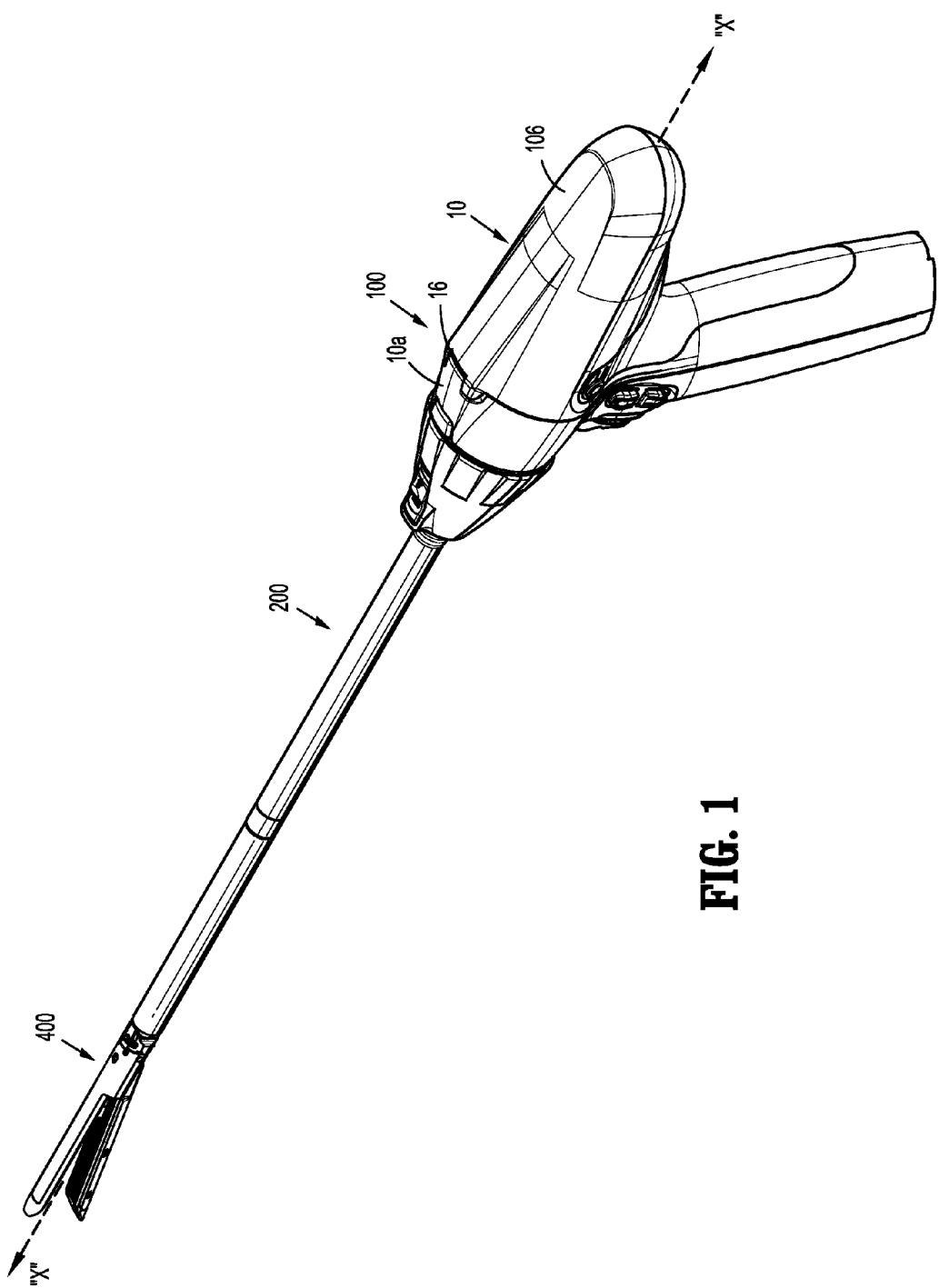
FIG. 1 is a perspective view of an electromechanical hand-held surgical device and adapter assembly, in accordance with an embodiment of the present disclosure, illustrating a connection thereof with an end effector.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand-held electromechanical instrument. The powered hand-held electromechanical instrument is configured for selective attachment of an end effector thereto. The end effector can be actuated and manipulated by the powered hand-held electromechanical surgical instrument.

As illustrated in FIG. 1, surgical device 100 is configured for selective connection with an adapter 200, and, in turn, adapter 200 is configured for selective connection with end effectors or single use loading units ("SULU's") 400.

Figure 2:
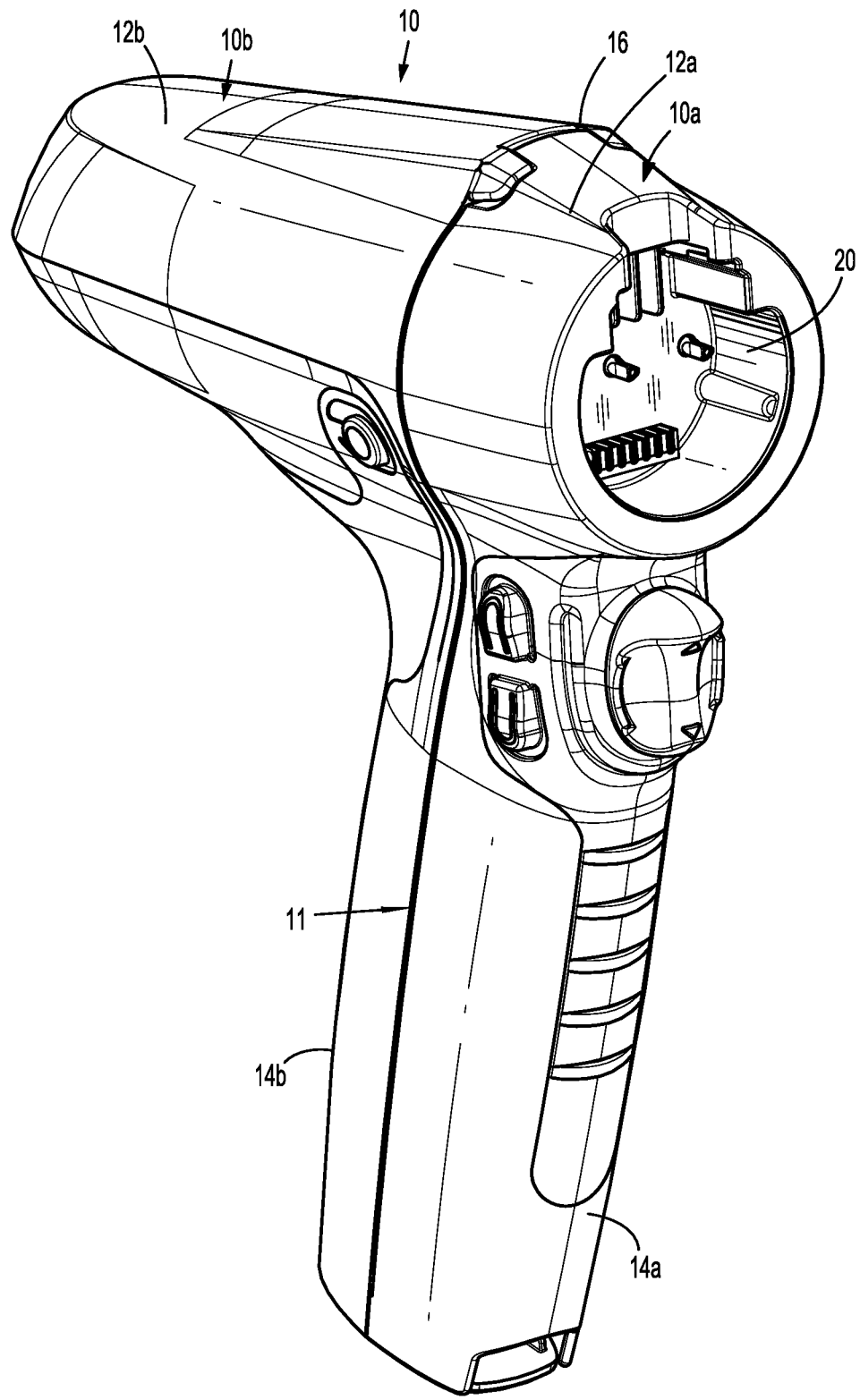
FIG. 2 is a perspective view of the outer shell housing of the electromechanical hand-held surgical device of FIG. 1.
Figure 3:
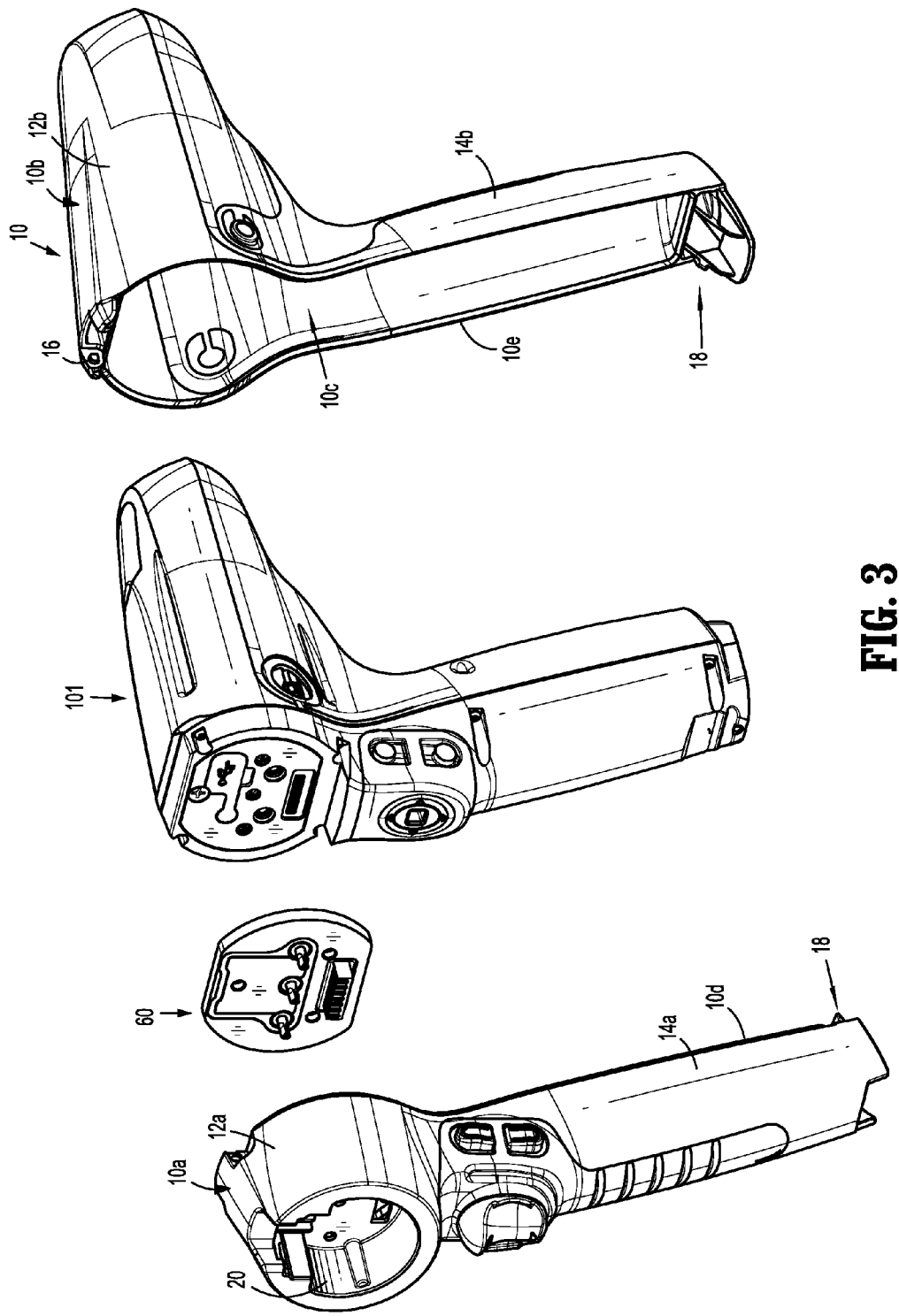
FIG. 3 is a front perspective view, with parts separated, of the outer shell housing of the electromechanical hand-held surgical device of FIGS. 1 and 2.

As illustrated in FIGS. 1-3, surgical device 100 includes a power-pack 101 configured to selectively control end effector 400, and an outer shell housing 10 configured to selectively receive and substantially encase power-pack 101. Power-pack 101 includes a battery, control circuitry and motors to actuate end effector 400. For a detailed explanation of the components of power-pack 101, see U.S. Provisional Patent Application No. 62/060,734, filed Oct. 7, 2014, now U.S. patent application Ser. No. 14/863,558, filed Sep. 24, 2015, (now U.S. Patent Application Publication No. 2016/0095585), the entire contents of which are incorporated herein by this reference.

Outer shell housing 10 includes a distal half-section 10a and a proximal half-section 10b pivotably connected to distal half-section 10a by a hinge 16 located along an upper edge of distal half-section 10a and proximal half-section 10b. Distal and proximal half-sections 10a, 10b are divided along a plane that traverses a longitudinal axis "X-X" of surgical device 100.

Distal half-section 10a includes a proximal facing edge 10d, and proximal half-section 10b includes a distal facing edge 10e (see FIG. 3). When distal and proximal half-sections 10a, 10b are joined, proximal facing edge 10d of distal half-section 10a and distal facing edge 10e of proximal half-section 10b define an interface 11 (see FIG. 2) along the perimeter of the proximal and distal facing edges 10d, 10e. At the same time, distal and proximal half-sections 10a, 10b define a shell cavity 10c therein in which power-pack 101 is selectively situated.

Outer shell housing 10 may also include a sterile barrier plate assembly 60 selectively supported in distal half-section 10a. Specifically, sterile barrier plate assembly 60 is disposed behind connecting portion 20 of distal half-section 10a and within shell cavity 10c of shell housing 10.

Each of distal and proximal half-sections 10a, 10b of outer shell housing 10 includes a respective upper shell portion 12a, 12b, and a respective lower shell portion 14a, 14b. Lower shell portions 14a, 14b define a snap closure feature 18 for selectively securing lower shell portions 14a, 14b to one another and for maintaining outer shell housing 10 in a closed condition.

When outer shell housing 10 is in a closed position, it is contemplated that interface 11 may employ a seal or gasket between the distal half-section 10a and the proximal half-section 10b to prevent undesired materials from being introduced into shell cavity 10c of outer shell housing 10 and in turn, to power-pack 101, or from contaminants escaping from shell cavity 10c and being introduced into a sterile surgical environment. As such, in embodiments, the proximal and distal facing edges 10d, 10e of distal and proximal half-sections 10a, 10b, respectively, may include a seal or gasket, as shown in FIG. 4.

Figure 4:
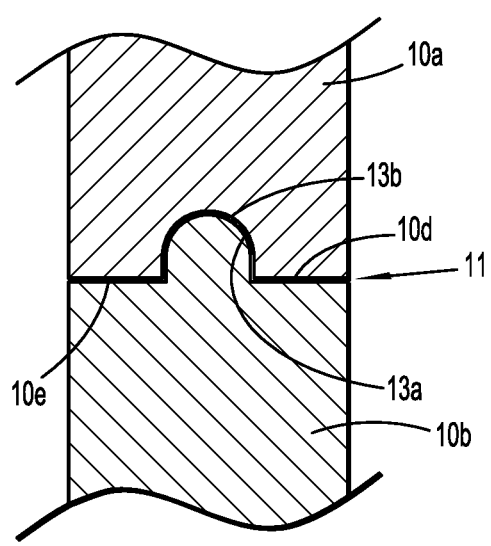
FIG. 4 is a cross-sectional view of an embodiment of an interface defined in the outer shell housing of the electromechanical hand-held surgical device of FIG. 1.

In particular, FIG. 4, which illustrates a cross-section of interface 11 along the longitudinal axis "X-X," shows a tongue and groove geometry in which the distal facing edge 10e of proximal half-section 10b defines a tongue 13a and the proximal facing edge 10d of distal half-section 10a defines a groove 13b configured and shaped to receive the tongue 13a. While a tongue and groove geometry is shown, it is contemplated that any suitable seal geometry may be used to provide a seal at interface 11.

In embodiments, distal half-section 10a and proximal half-section 10b of outer shell housing 10 may be fabricated from a polycarbonate or similar polymer. In embodiments, the material may be a transparent rigid polymer. In embodiments, distal half-section 10a and proximal half-section 10b of outer shell housing 10 may be overmolded onto a substrate. It is contemplated that the seal, as shown by example of the tongue and groove geometry in FIG. 4, may also be fabricated from a polycarbonate or similar polymer during this process, similar to distal half-section 10a and proximal half-section 10b.

With reference to FIGS. 5A-5F, it is further contemplated that an external seal insert or gasket 40 may be used alongside or in place of (see FIG. 5F) the interface configuration shown in FIG. 4 to provide a sterile barrier between power-pack 101 and an operating room. In embodiments, gasket 40 may be disposable or reposable up to a predetermined amount of uses and may include one or more antimicrobial substances incorporated therein.

It is contemplated that gasket 40 may be configured to compress into the geometry of interface 11, such as, for example, the tongue and groove geometry shown in FIGS. 5A-5E. To that end, gasket 40 may be a low viscosity and low durometer material to allow gasket 40 to conform to the geometry of interface 11.

Gasket 40 includes a body 40a having a first side 41a and a second side 41b. In embodiments, first side 41a is located adjacent distal half-section 10a of outer shell housing 10 and second side 41b is located adjacent proximal half-section 10b of outer shell housing 10. However, in embodiments, the reverse orientation is possible. In order to secure gasket 40 to interface 11, it is contemplated that first and second sides 41a, 41b may include a fixation mechanism, such as, for example, an adhesive or any suitable fastener.

In embodiments, gasket 40 may include a reinforcing member, such as, for example, a rod 42 as shown in FIGS. 5C and 5E. Rod 42 may be embedded into the body 40a of gasket 40. In embodiments, rod 42 may be configured to add rigidity to gasket 40.

In embodiments, where interface 11 includes surface geometry or topography, as shown for example in FIGS. 5C and 5E, rod 42 may be configured and sized to be integrated into the surface geometry of interface 11. For example, in FIGS. 5C and 5E, groove 13b of distal half-section 10a of outer shell housing 10 may include a diameter "D1" and rod 42 may include a diameter "D2," where the diameter "D1" is equal to the diameter "D2." As such, when the distal and proximal half-sections 10a, 10b are approximated, tongue 13a of proximal half-section 10b urges rod 42 of gasket 40 towards groove 13b such that rod 42 of gasket 40 may be nested within groove 13b while body 40a of gasket 40 conforms to the surrounding geometry of interface 11.

With specific reference to FIGS. 5A-5C and 5F, in embodiments, gasket 40 may be pre-formed to the geometry of interface 11. For example, as shown in FIGS. 5B, 5C, and 5F, gasket 40 may include a substantially H-shaped cross-sectional profile. It is contemplated that the pre-formed gasket 40 may be easier to locate on the proximal or distal facing edges 10d, 10e of distal and proximal half-sections 10a, 10b, respectively.

In embodiments as shown in FIG. 5A, gasket 40 may include a line of reduced thickness or a perforation line 40b defined in body 40a such that after gasket 40 is located in interface 11, a flange portion 40c of gasket 40 may be removed along the perforation line 40b.

It is contemplated that various methods and devices may be employed when locating gasket 40 on the interface 11 between distal and proximal half-sections 10a, 10b. In embodiments, medical personnel, such as, for example, a nurse may install the gasket 40 with their hands. To that end, it is contemplated that gasket 40 may include a removable coating, such as, for example, a film 44 on each of first side 41a and second side 41b (see FIG. 8) of gasket 40.

In operation, after removing the film 44 from one of the sides of gasket 40, for example, from side 41b, the medical personnel would place side 41b against the distal facing edge 10e of proximal half-section 10b of outer shell housing 10. With power-pack 101 inserted into shell cavity 10c of shell housing 10, the medical personnel would then remove the remaining film (not expressly shown) from the opposite side, for example, from side 41a, and approximate the distal and proximal half-sections 10a, 10b of outer shell housing 10.

Figure 7:
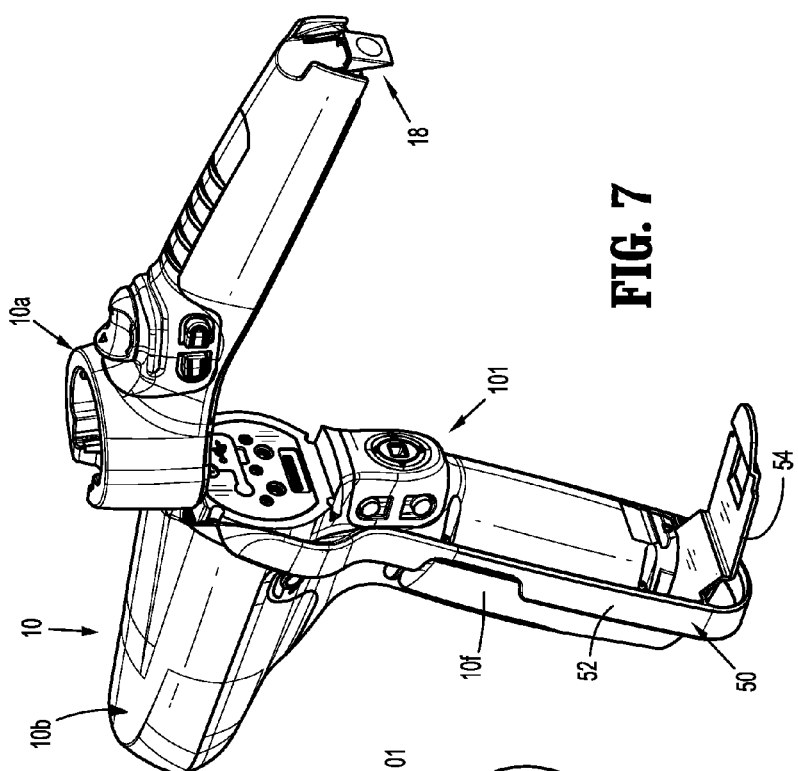
FIG. 7 is a perspective view illustrating the power-pack nested into the outer shell housing of the hand-held surgical device.
Figure 6:
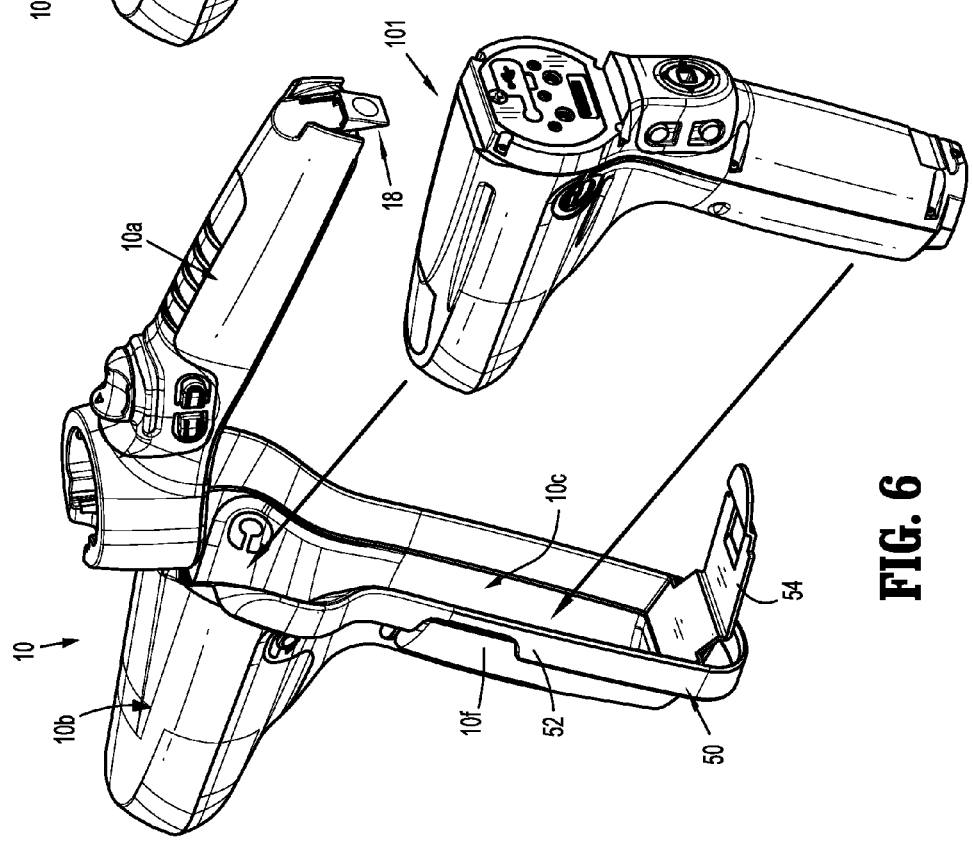
FIG. 6 is a perspective view illustrating insertion of a power-pack into an outer shell housing of an electromechanical hand-held surgical device.
Figure 8:
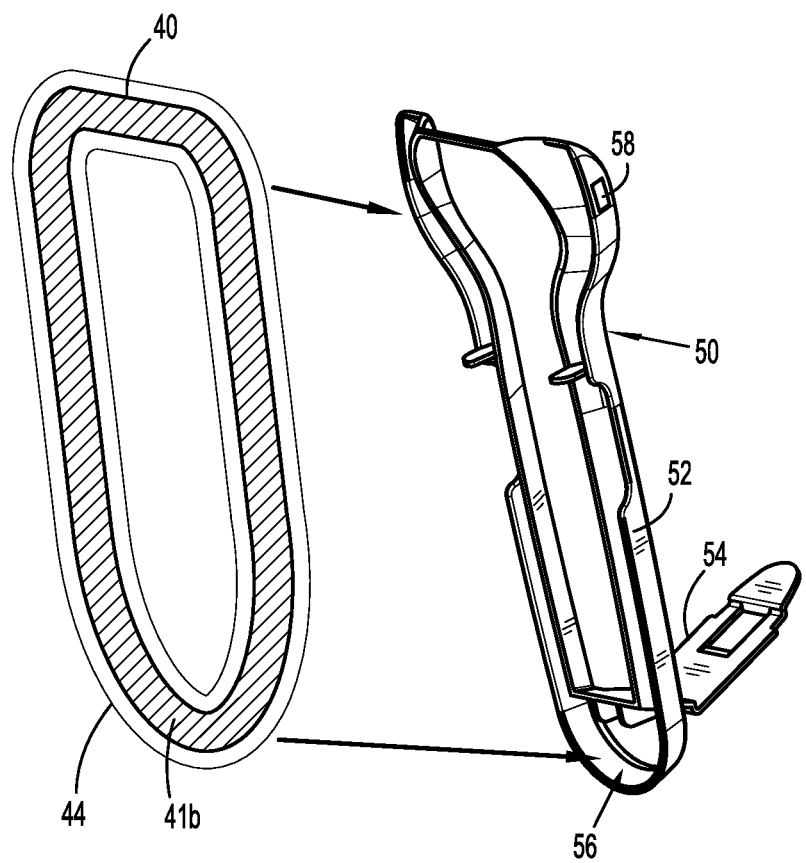
FIG. 8 is a perspective view illustrating insertion of a gasket into an insertion guide for use with the hand-held surgical device.

Alternatively, the gasket 40 may be incorporated into an insertion guide 50, as detailed below, prior to being located in interface 11. With reference to FIGS. 6-8, an insertion guide 50 configured and shaped to seat on and entirely surround the distal facing edge 10e (see FIG. 3) of proximal half-section 10b may be provided with surgical device 100. Insertion guide 50 is configured to space apart power-pack 101 and an outer surface 10f (see FIGS. 6 and 7) of outer shell housing 10 to prevent undesired contact between power-pack 101 and outer surface 10f.

Insertion guide 50 includes a body portion 52 having a substantially U-shaped transverse cross-sectional profile, and a stand-off 54 extending from a bottom of body portion 52. Stand-off 54 is configured to engage snap closure feature 18 of each of lower shell portions 14a, 14b of respective distal and proximal half-sections 10a, 10b of shell housing 10.

In use, when body portion 52 of insertion guide 50 is seated on distal facing edge 10e of proximal half-section 10b, snap closure feature 18 of lower shell portion 14a of distal half-section 10a engages a first end of stand-off 54, and snap closure feature 18 of lower shell portion 14b of proximal half-section 10b engages a first end of stand-off 54.

Figure 9:
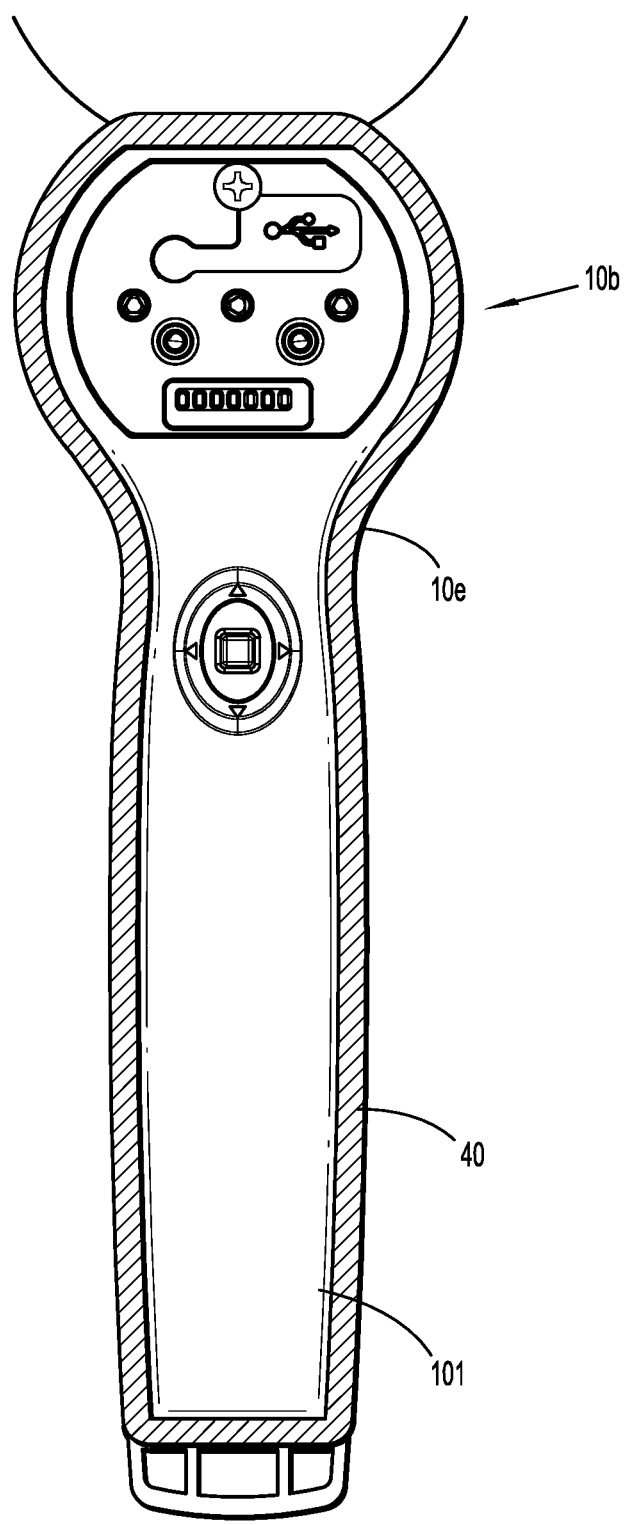
FIG. 9 is a front view illustrating the power-pack nested into the outer shell housing and the gasket located on the interface defined in the outer shell housing of the hand-held surgical device.

Body portion 52 also includes a track 56 on a proximal facing side 58 of insertion guide 50. Track 56 is configured to engage the distal facing edge 10e of proximal half-section 10b. In embodiments, track 56 may also be configured to receive gasket 40, as shown in FIG. 8. It is contemplated that incorporating gasket 40 into track 56 of the insertion guide 50 may simplify the process of locating gasket 40 in interface 11 as well as promote improved sterility of gasket 40, by limiting the amount of time that gasket 40 is handled by medical personnel. Once gasket 40 is positioned in the desired location, it is contemplated that gasket 40 may be released from insertion guide 50 using a mechanical release, such as, for example, a latch or ejector 58 (see FIG. 8) or through gravity, leaving gasket 40 on the distal facing edge 10e of proximal half-section 10b of outer shell housing 10 (see FIG. 9).

In operation, gasket 40 is pressed into track 56 of insertion guide 50 and film 44 is removed from second side 41b. Next, with a new and/or sterile outer shell housing 10 in an open configuration (i.e., distal half-section 10a separated from proximal half-section 10b, about hinge 16), and with insertion guide 50, including gasket 40, in place against the distal edge of proximal half-section 10b of shell housing 10, power-pack 101 is inserted into shell cavity 10c of shell housing 10. With power-pack 101 inserted into shell cavity 10c of shell housing 10, insertion guide 50 is removed from proximal half-section 10b, leaving behind gasket 40 on the distal facing edge 10e of proximal half-section 10b. Removing the film (not expressly shown) on first side 41a of gasket 40, the distal half-section 10a of outer shell housing 10 is pivoted, about hinge 16, to a closed configuration. In the closed configuration, snap closure feature 18 of lower shell portion 14a of distal half-section 10a engages snap closure feature 18 of lower shell portion 14b of proximal half-section 10b. In the closed configuration, gasket 40 compresses and migrates to fill in the geometry of interface 11 as shown in FIGS. 5A-5F.

In operation, following a surgical procedure, snap closure feature 18 of lower shell portion 14a of distal half-section 10a is disengaged from snap closure feature 18 of lower shell portion 14b of proximal half-section 10b, and distal half-section 10a is pivoted, about hinge 16, away from proximal half-section 10b to open shell housing 10. With outer shell housing 10 open, power-pack 101 is removed from shell cavity 10c of outer shell housing 10 (specifically from proximal half-section 10b of shell housing 10), and outer shell housing 10 is discarded. Depending on the type of gasket 40 used, gasket 40 is either discarded with outer shell housing 10 or reused after being sterilized. Power-pack 101 is then disinfected and cleaned. Power-pack 101 is not to be submerged or sterilized.

Figure 10:
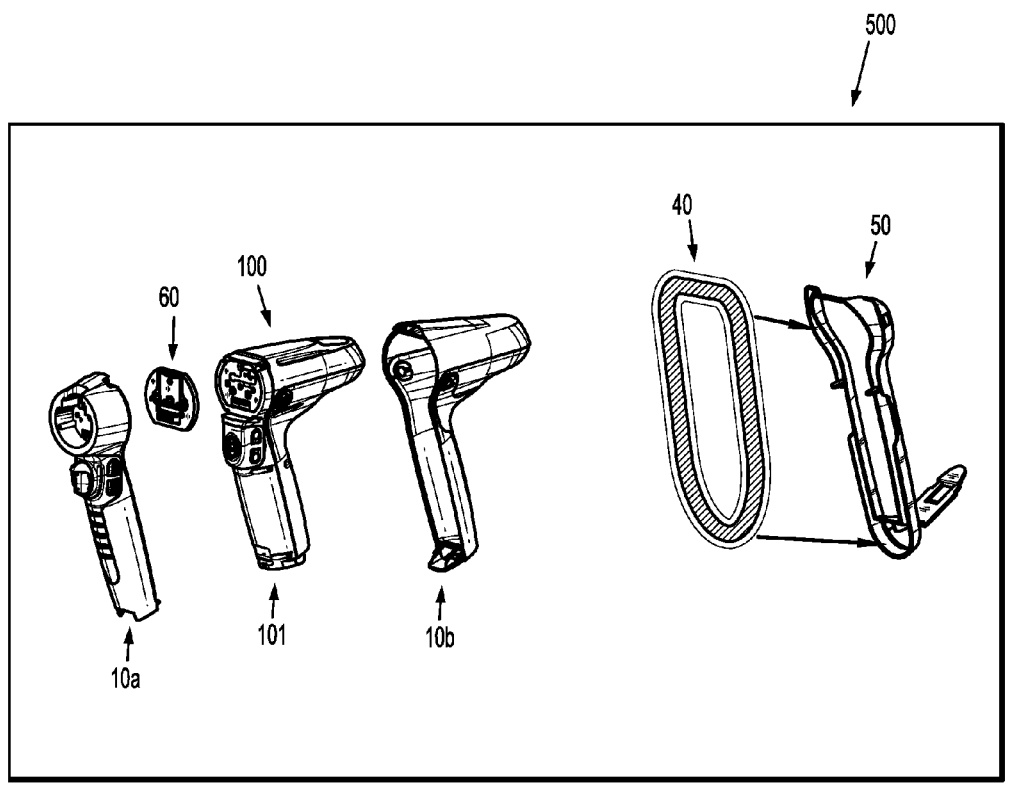
FIG. 10 is a kit including the electromechanical hand-held surgical device according to FIG. 1, the gasket, and the insertion guide in accordance with the present disclosure.

In accordance with the present disclosure, it is further contemplated that a kit 500 as shown in FIG. 10 may be provided. Kit 500 may include the electromechanical surgical device 100 having the distal and proximal half-sections 10a, 10b of outer shell housing 10, the sterile barrier plate assembly 60, and the power-pack 101. The kit 500 may also include the gasket 40 and the insertion guide 50. The kit 500 may further include instructions for the assembly of the electromechanical surgical device 100, the use of the electromechanical surgical device 100, and a package, container or box configured to retain the same.

Figure 11A:
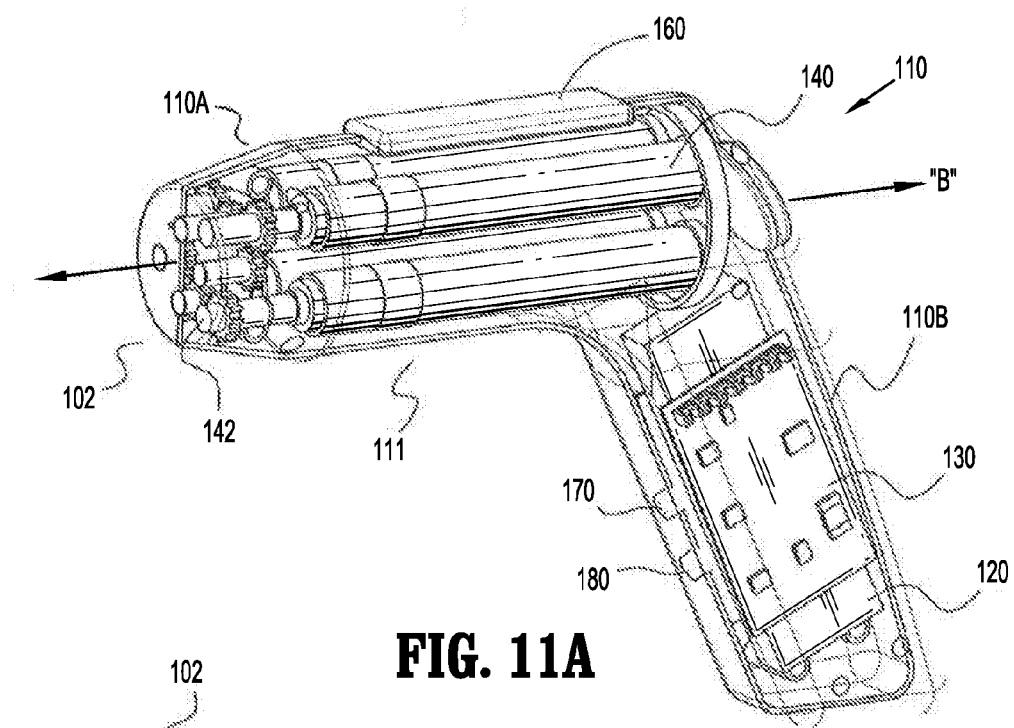
FIGS. 11A and 11B illustrate perspective views of a reusable surgical instrument module, in accordance with an embodiment of the present disclosure.
Figure 11B:
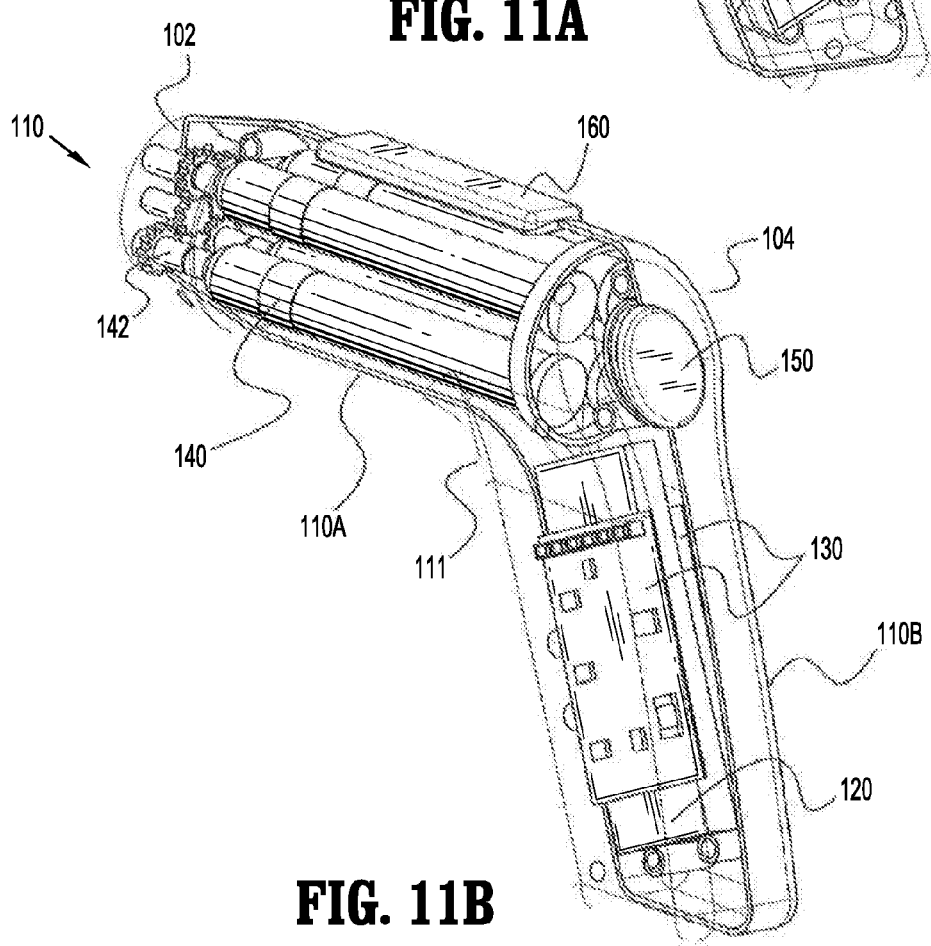

Referring to FIGS. 11A and 11B, illustrated is an embodiment of a reusable surgical instrument module 110, which shares similarities with power-pack 101 of FIGS. 1-3. Instrument module 110 defines an upper instrument module half 110A and a lower instrument module half 110B, upper instrument module half 110A defining a longitudinal axis "B." Instrument module 110 also includes an inner housing shell 111 for incorporating a plurality of components therein, as described below.

Upper instrument module half 110A includes at least one motor 140, as well as a display screen 160. At least one motor 140 is disposed within inner housing shell 111. A distal end 102 of upper instrument module half 110A is configured to receive an end effector assembly. The end effector assembly may be at least one of jaw members, a clip applier, vessel sealing devices, circular stapling devices, dissectors, retractors, cutters, graspers, and drills.

Lower instrument module half 110B includes a battery 120 (or energy source) and at least one control board 130. Battery 120 and at least one control board 130 are disposed within inner housing shell 111. Lower instrument module half 110B is configured to be gripped by a user, such as surgeon, during a surgical procedure. Additionally, upper instrument module half 110A and lower instrument module half 110B may combine to form a substantially L-shaped or pistol-grip configuration.

At least one control board 130 is connected, on the one hand, electrically to battery 120, and, on the other hand, to at least one motor 140. To this end, electric contacts (not shown) are provided on an upper side of battery 120 for establishing an electric connection with at least one control board 130. Additionally, at least one control board 130 electrically communicates with at least one processor (not shown) for enabling flow of electrosurgical energy between the energy source (e.g., battery 120) and each motor 140.

Each motor 140 is configured to include, for instance, a drive shaft 142. Drive shaft 142 defines an operative axis of rotation "B." Each motor 140 is configured to actuate a function or operation of an end effector assembly (not shown), including but not limited to, articulating, rotating, closing of the jaw members, ejecting fasteners, cutting, and the like.

Instrument module 110 may include a speaker 150 (see FIG. 11B), at a proximal end 104 thereof, for providing feedback information related to tissue parameters and surgical instrument parameters measured during a surgical procedure. Speaker 150 may be used to provide audible feedback. Audible feedback may be used in conjunction with or in lieu of the visual outputs.

Instrument module 110 may include display screen 160 disposed therein displaying information related to tissue parameters and surgical instrument parameters measured during a surgical procedure. Display screen 160 may be configured to provide the surgeon with a variety of suitable output information. Display screen 160 may include at least one of numerical indicators and color indicators.

Instrument module 110 may also include a clamp button 170 and a return button 180. Clamp button 170 may be configured to actuate an end effector assembly (not shown) connected to distal end 102 of instrument module 110 to a first position. End effector assembly may be a pair of jaw members for clamping tissue in the first position. Return button 180 may be configured to return the jaw members to an open, unclamped position (or second position).

Figure 12:
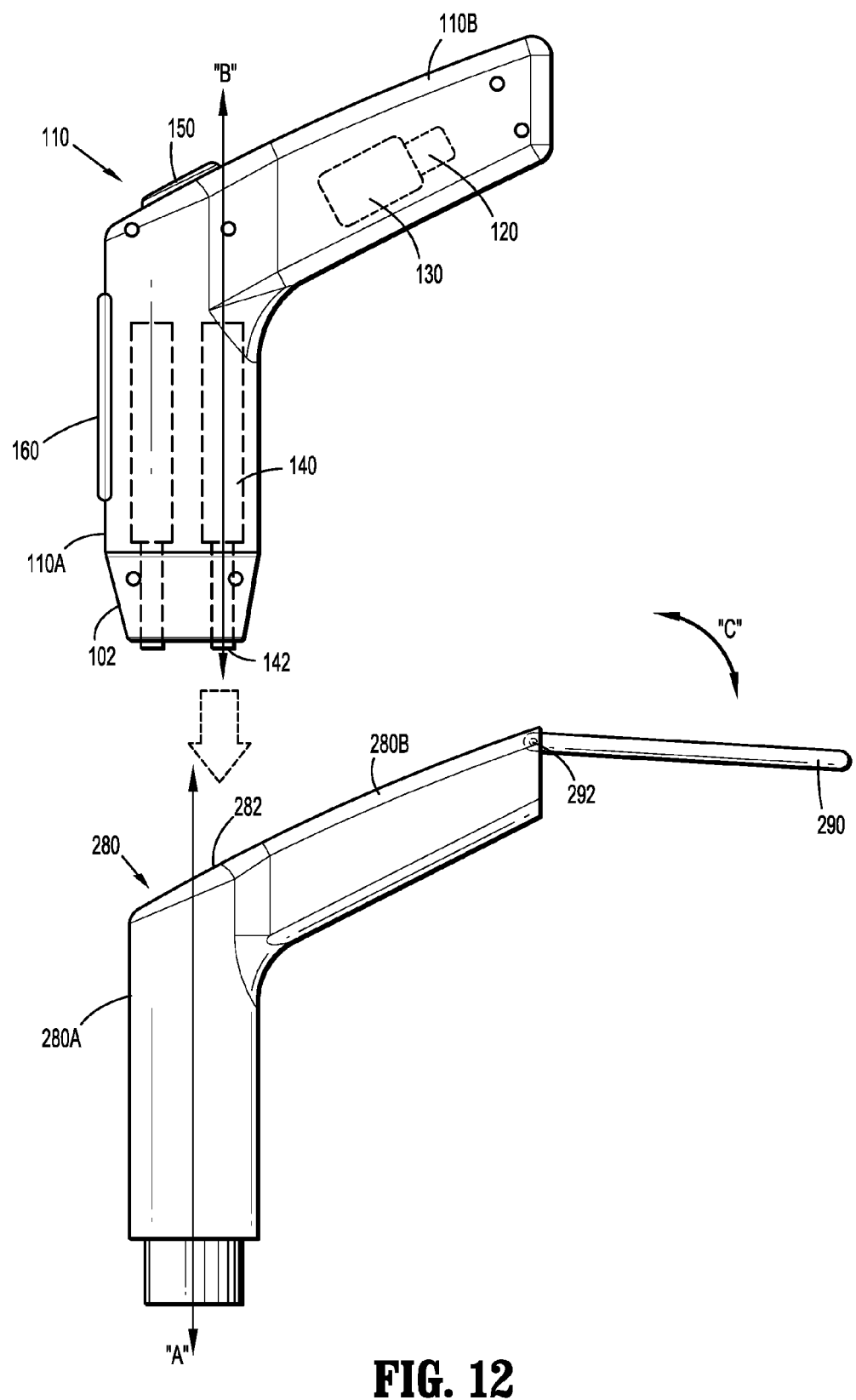
FIG. 12 illustrates a reusable surgical instrument module inserted into an outer housing shell having a hinged instrument cover shell, in accordance with an embodiment of the present disclosure.

Referring to FIG. 12, a method of inserting a reusable surgical instrument module 110 into an outer housing shell 280 having a hinged instrument cover shell 290, in accordance with an embodiment of the present disclosure is presented.

Outer housing shell 280 defines a cavity 282 therein. Outer housing shell 280 defines an upper outer housing half 280A and a lower outer housing half 280B. Upper outer housing half 280A defines a longitudinal axis "A" extending therethrough. Outer housing shell 280 also includes instrument shell cover 290 connected to lower outer housing half 280B via a hinged connection 292. Instrument shell cover 290 may rotate or pivot in direction "C" after instrument module 110 has been fully inserted into outer housing shell 280, as described below. In accordance with an embodiment of the present disclosure, outer housing shell 280 may be devoid of movable switches.

In operation or use, instrument module 110 is inserted into cavity 282 of outer housing shell 280 in such a manner that operative axis "B" of at least one motor 140 is substantially parallel to longitudinal axis "A" of upper outer housing half 280A. Stated differently, instrument module 110 is configured to be inserted into reusable outer housing shell 280, such that instrument module 110 is inserted and extracted along an axis of operation of at least one motor 140 or along longitudinal axis "B." Upper instrument module half 110A is configured to underlie or nest upper outer housing half 280A, whereas lower instrument module half 110B is configured to underlie or nest lower outer housing half 280B. Once instrument shell 110 is fully inserted into outer housing shell 280, instrument shell cover 290 is rotated, in direction "C," in order to create a secure seal with outer housing shell 280.

Following a surgical procedure, instrument shell cover 290 is opened and instrument module 110 is withdrawn from or removed from cavity 282 of outer housing shell 280 such that outer housing shell 280 and shell cover 290 may be cleaned in accordance with methods and procedures known in the art, for example, sterilizing, autoclaving, steam cleaning, wiping with cleaning products/solvents and the like. Thus, outer housing shell 280 and shell cover 290 may be cleaned or sterilized without compromising instrument module 110 inserted therein. Once cleaning or sterilization has been completed, instrument module 110 may be re-introduced into cavity 282 of outer housing shell 280 prior to performing a further surgical procedure.

Figure 13:
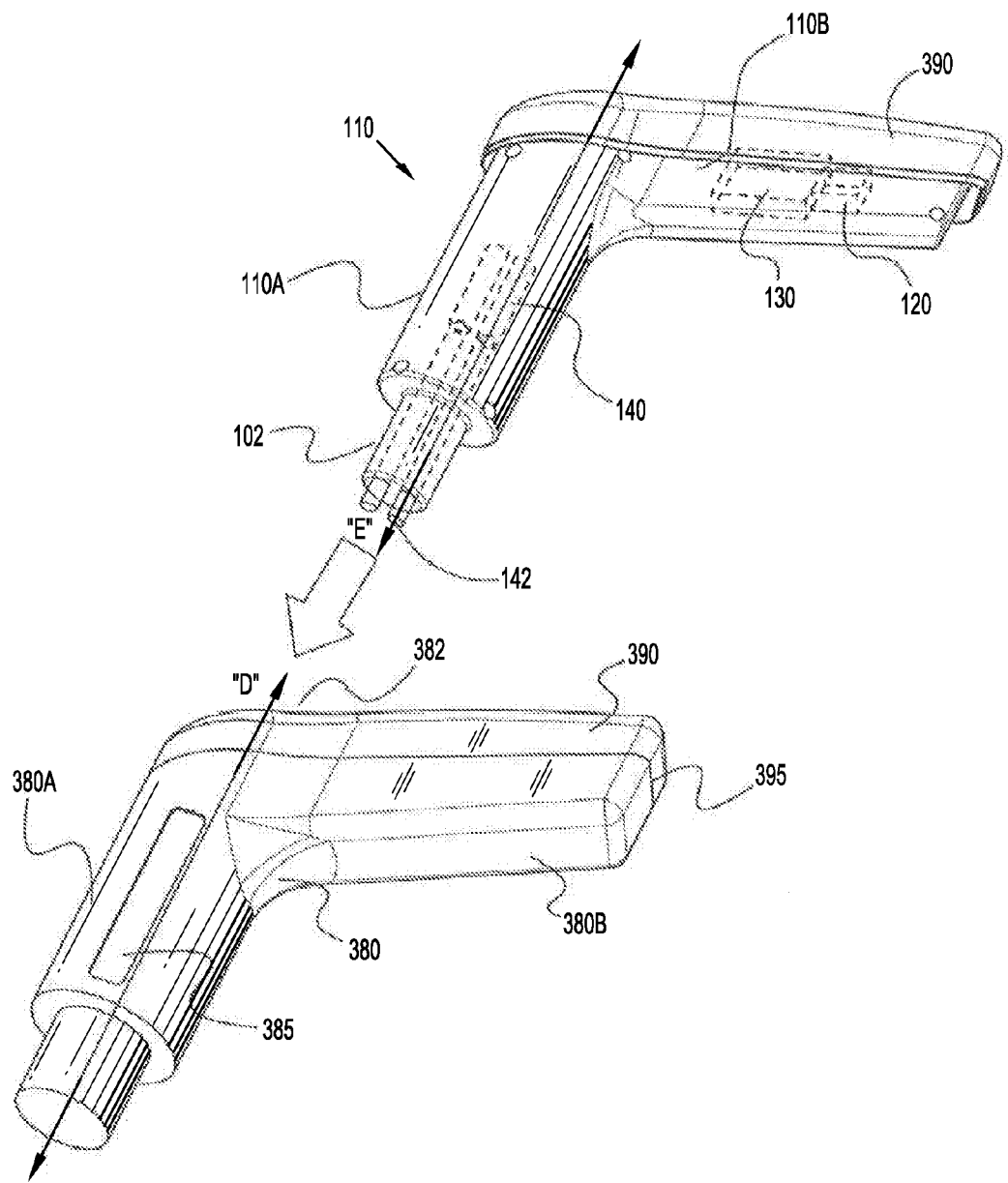
FIG. 13 illustrates a reusable surgical instrument module inserted into an outer housing shell having a snapable instrument cover shell, in accordance with another embodiment of the present disclosure.

Referring to FIG. 13, a method of inserting a reusable surgical instrument module 110 into an outer housing shell 380 having a snapable instrument cover shell 390, in accordance with another embodiment of the present disclosure is illustrated.

Outer housing shell 380 defines a cavity 382 therein. Outer housing shell 380 defines an upper outer housing half 380A and a lower outer housing half 380B. Upper outer housing half 380A defines a longitudinal axis "D" extending therethrough. Lower outer housing half 380B of outer housing shell 380 may connect or attach to instrument shell cover 390 via, for example, a snapable mechanism including fasteners (not shown). Additionally, a clear viewing window 385 may be constructed so that it overlays a display screen (e.g., as described above with reference to FIGS. 11A and 11B). Viewing window 385 is designed for viewing the display screen disposed therein displaying information related to tissue parameters and surgical instrument parameters measured during a surgical procedure.

In accordance with the present disclosure, it is contemplated that outer housing shell 380 (as well as outer housing shells 180, 280) may be fabricated from a translucent or transparent material, such as, for example, a polycarbonate resin thermoplastic. As so constructed, indicia from display screen 160 of instrument module 110 or the like. It is further contemplated that at least a portion of outer housing shell 380 may be translucent or transparent.

In operation or use, instrument module 110 is inserted into cavity 382 of outer housing shell 380 in such a manner that operative axis "E" of at least one motor 140 (or of at least one drive shaft 142) is substantially parallel to longitudinal axis "D" of upper outer housing half 110A. Stated differently, instrument module 110 is configured to be inserted into instrument outer housing shell 380, such that instrument module 110 is inserted and extracted along an axis of operation of at least one motor 140, or along longitudinal axis "E." Upper instrument module half 110A is configured to underlie or nest upper outer housing half 380A, whereas lower instrument module half 110B is configured to underlie or nest lower outer housing half 380B. Once instrument shell cover 390 is attached to a portion of lower outer housing half 380B, instrument module 110 is inserted into outer housing shell 380 such that upper outer housing half 380A and the remaining portion of the lower outer housing half 380B lock or secure or seal with instrument shell cover 390 along connection region 395.

Following a surgical procedure, instrument shell cover 390 is withdrawn or unsnapped from lower outer housing half 380B (at connection region 395) and instrument module 110 is withdrawn from or removed from cavity 382 of outer housing shell 380 such that outer housing shell 380 and shell cover 390 may be cleaned in accordance with methods and procedures known in the art. Thus, outer housing shell 380 may be cleaned or sterilized without compromising instrument module 110 inserted therein. Once cleaning or sterilization has been completed, instrument module 110 may be re-introduced into cavity 382 of outer housing shell 380 prior to performing a further surgical procedure.

Figure 14:
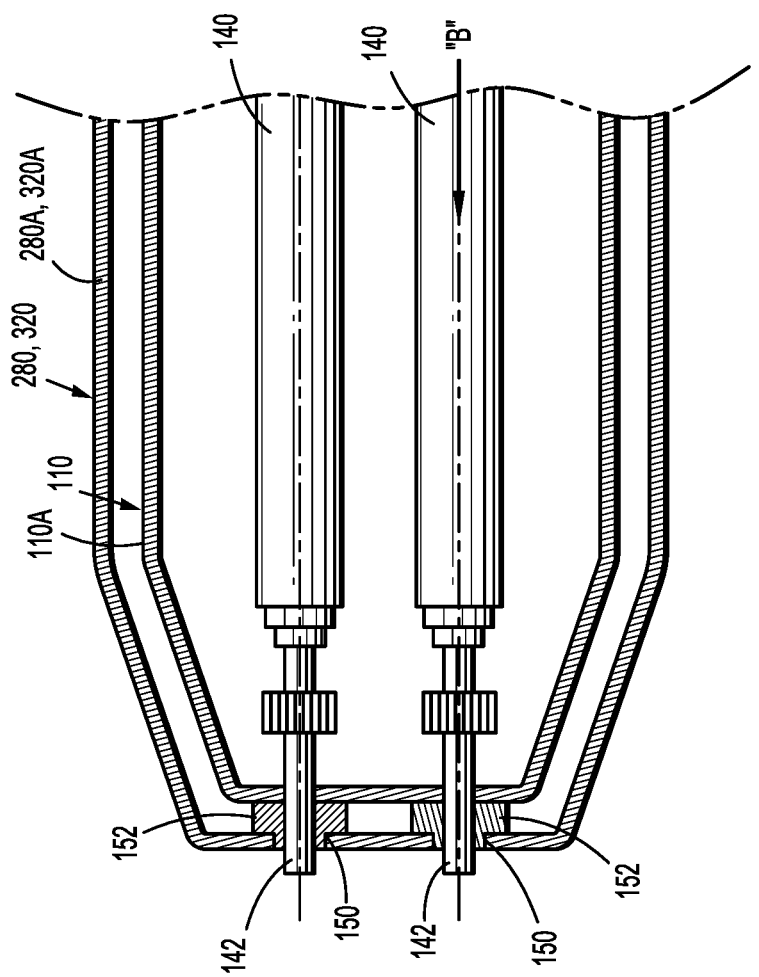
FIG. 14 is an enlarged, schematic, longitudinal cross-sectional view illustrating the reusable surgical instrument module inserted into the outer housing shell, and showing seals disposed about drive shafts of the reusable surgical instrument module.

Turning now to FIG. 14, in accordance with the present disclosure, it is contemplated that outer housing shell 280, 380 may define a plurality of apertures 150 through which each drive shaft 142 passes. A seal 152 is provided in each aperture 150 and is supported therein so as to remain with outer housing shell 280, 380 during insertion/retraction of instrument module 110 therein/therefrom. Seals 152 may take the form of O-rings or the like, and may be constructed from a resilient, polymeric material, such as, for example, rubber. Seals 152 are configured and dimensioned to establish a fluid-tight seal between outer housing shell 280, 380 and drive shafts 142. Additionally, seals 152 are configured and dimensioned to permit drive shafts 142 to rotate. In use, when shell covers 290, 390 are closed against respective outer housing shells 280, 380, a force is exerted against instrument module 110, substantially along or in direction "B", to thereby press a distal surface of upper instrument module half 110A against seals 152 and establish a fluid-tight seal against an outer surface of drive shafts 142.

It will be understood that various modifications may be made to the embodiments disclosed above. For example, gasket 40 of FIGS. 1-10 may be located using a specialized tool or track in place of the insertion guide 50. It its contemplated that the specialized tool or track may be sterilized using an autoclave or similar device.

Therefore, the above description should not be construed as limiting, but merely as exemplifications of embodiments.

Those skilled in the art will envision other modifications within the scope and spirit of the present disclosure.

What is claimed is:

1. A hand-held electromechanical surgical device comprising:
   a power-pack configured to selectively control a surgical accessory;
   an outer shell housing including a distal half-section and a proximal half-section, the distal half-section and the proximal half-section together defining a cavity configured to selectively encase substantially the entire power-pack therein; and
   a gasket located between the distal half-section and the proximal half-section of the outer shell housing, the gasket configured to create a seal between the distal half-section and the proximal half-section and to provide a sterile barrier between the power-pack and an environment outside the outer shell housing.

2. The electromechanical surgical device according to claim 1, wherein the distal half-section includes a proximal facing edge and the proximal half-section includes a distal facing edge, wherein in a first position, the proximal facing edge and the distal facing edge are spaced apart, and wherein in a second position, the proximal facing edge and the distal facing edge are approximated defining an interface therebetween.

3. The electromechanical surgical device according to claim 2, wherein the gasket is disposed at the interface defined between the distal facing edge of the proximal half-section of the outer shell housing, and the proximal facing edge of the distal half-section of the outer shell housing.

4. The electromechanical surgical device according to claim 2, wherein the proximal facing edge of the distal half-section of the outer shell housing defines a groove configured to receive the gasket.

5. The electromechanical surgical device according to claim 4, wherein the distal facing edge of the proximal half-section defines a protrusion configured to engage the gasket, wherein in the second position, at least a portion of the gasket is nested in the groove defined in the distal half-section when the proximal half-section and the distal half-section are approximated.

6. The electromechanical surgical device according to claim 5, wherein the gasket includes a reinforcing member configured to strengthen the seal between the distal half-section and the proximal half-section.

7. The electromechanical surgical device according to claim 6, wherein the reinforcing member is configured to be nested in the groove defined in the distal half-section of the outer shell housing when the proximal half-section and the distal half-section are approximated.

8. A method of assembling a hand-held electromechanical surgical device, comprising:
   installing a gasket onto a proximal half-section of an outer shell housing of a hand-held electromechanical surgical device;
   inserting a power-pack into a receiving cavity of the outer shell housing while maintaining a sterility of the outer shell housing; and
   closing the outer shell housing by approximating the proximal half-section with a distal half-section of the outer shell housing to substantially entirely encase the power-pack within the outer shell housing, the gasket creating a seal between the distal half-section and the proximal half-section and providing a sterile barrier between the power-pack and an environment outside the outer shell housing.

9. The method according to claim 8, wherein installing the gasket onto the outer shell housing comprises:
   removing a removable coating from a second side of the gasket; and
   positioning the second side of the gasket on the proximal half-section of the outer shell housing.

10. The method according to claim 9, wherein installing the gasket onto the outer shell housing comprises:
    inserting the gasket into a track defined in an insertion guide configured to guide the insertion of the power-pack into the receiving cavity of the outer shell housing;
    positioning the insertion guide onto the proximal half-section of the outer shell housing such that the gasket is located on a distal facing edge of the proximal half-section of the outer shell housing; and
    releasing the gasket from the track defined in the insertion guide such that when the insertion guide is removed from the proximal half-section of the outer shell housing, the gasket remains located on the distal facing edge of the proximal half-section of the outer shell housing.

11. A kit comprising:
    a power-pack;
    an electromechanical surgical device including an outer shell housing having a distal half-section and a proximal half-section, the distal half-section and the proximal half-section together defining a cavity configured to selectively encase substantially the entire power-pack therein; and
    an insertion guide, the insertion guide locatable on the distal facing edge of the proximal half-section of the outer shell housing, the insertion guide configured to shield an outer surface of the outer shell housing from the power-pack when the power-pack is being inserted into the cavity of the outer shell housing.

12. The kit according to claim 11, wherein the insertion guide includes a body defining a track, the track configured to engage the distal facing edge of the proximal half-section of the outer shell.

13. The kit according to claim 12, further including a gasket, wherein the gasket is positioned in the track of the insertion guide, such that when the insertion guide is disposed on the distal facing edge of the proximal half-section of the outer shell housing, the gasket is disposed on the distal facing edge of the proximal half-section of the outer shell housing.

14. The kit according to claim 13, wherein the insertion guide includes a mechanical release configured to release the gasket from the track therein.

* * * * *